United States Patent [19]

Compton et al.

[11] Patent Number: 5,535,810
[45] Date of Patent: Jul. 16, 1996

[54] CAST ORTHOPAEDIC IMPLANT AND METHOD OF MAKING SAME

[75] Inventors: Richard C. Compton; Leslie N. Gibertson, both of Warsaw, Ind.

[73] Assignee: Zimmer, Inc., Warsaw, Ind.

[21] Appl. No.: 508,806

[22] Filed: Jul. 28, 1995

[51] Int. Cl.$^6$ .................................................. B22D 19/00
[52] U.S. Cl. .............................. 164/35; 164/45; 164/97; 164/98
[58] Field of Search .................................. 164/97, 98, 35, 164/516, 34, 36, 45

[56] References Cited

U.S. PATENT DOCUMENTS

| | | | |
|---|---|---|---|
| 4,600,546 | 7/1986 | Grundei | 264/59 |
| 4,722,870 | 2/1988 | White | 428/621 |
| 4,781,721 | 11/1988 | Grundei | 623/16 |
| 5,016,702 | 5/1991 | Ahlers | 164/34 |
| 5,042,560 | 8/1991 | Ahlers | 164/34 |
| 5,178,201 | 1/1993 | Ahlers | 164/34 |
| 5,236,457 | 8/1993 | Devanathan | 623/16 |

*Primary Examiner*—Jack W. Lavinder
*Assistant Examiner*—Randolph S. Herrick
*Attorney, Agent, or Firm*—Todd A. Dawson

[57] ABSTRACT

A method of forming a cast orthopaedic implant having a porous surface layer is disclosed. The method includes placing a porous layer on a wax replica of the implant such that a portion of the pores of the layer are filled with the wax material. The wax replica and porous surface layer are coated by a ceramic material consistent with investment casting technology. The ceramic material fills the remainder of the pores of the porous layer. After the ceramic material is solidified, the wax material is melted away leaving a cavity within the ceramic material. The pores once filled by wax are now exposed and extend into the cavity. A molten metal is poured into the cavity and partially melts the exposed porous layer to form a melt bond with the molten metal. When the metal is cooled, the ceramic material is stripped away exposing the portion of the porous layer previously filled with the ceramic medium.

9 Claims, 3 Drawing Sheets

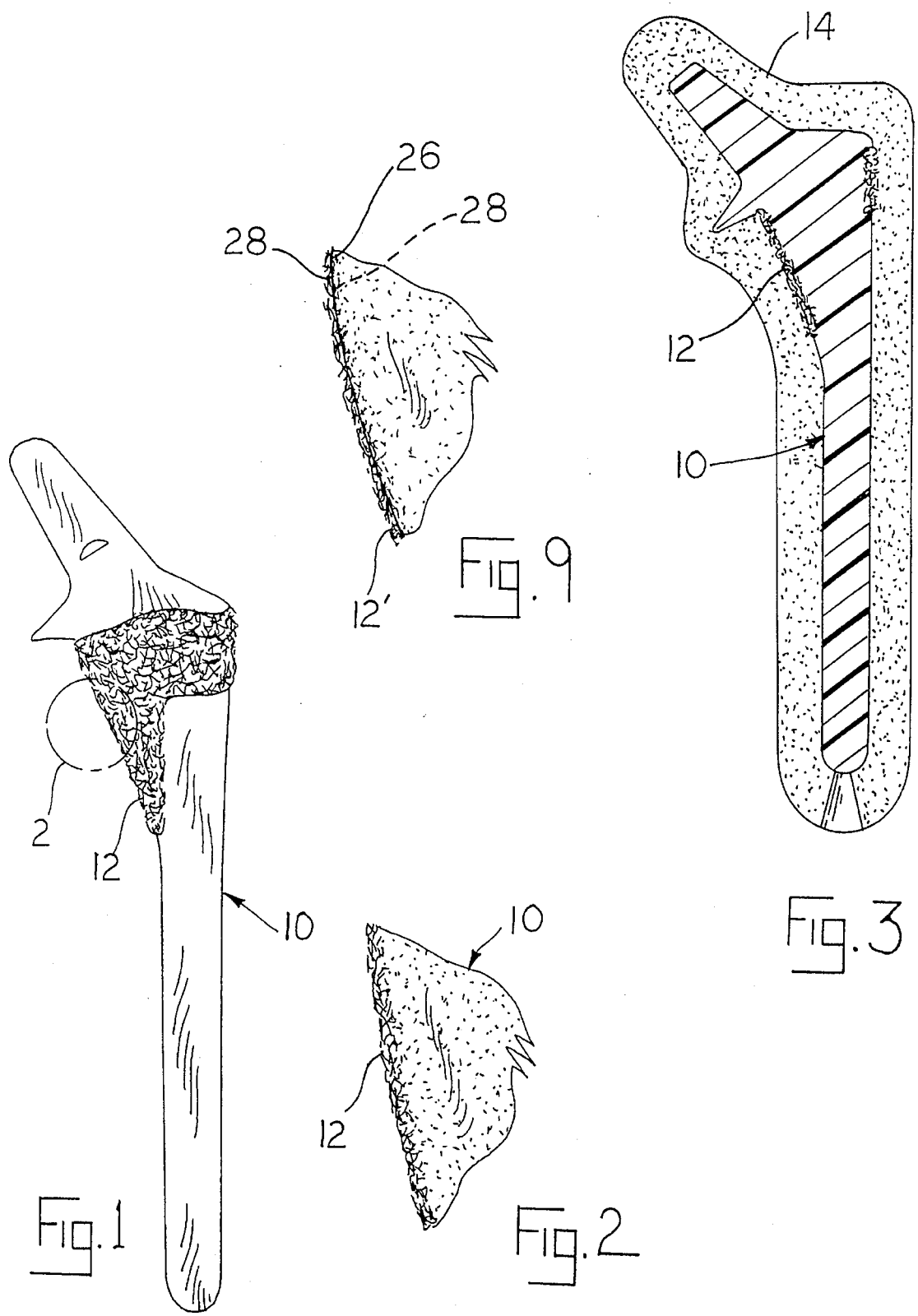

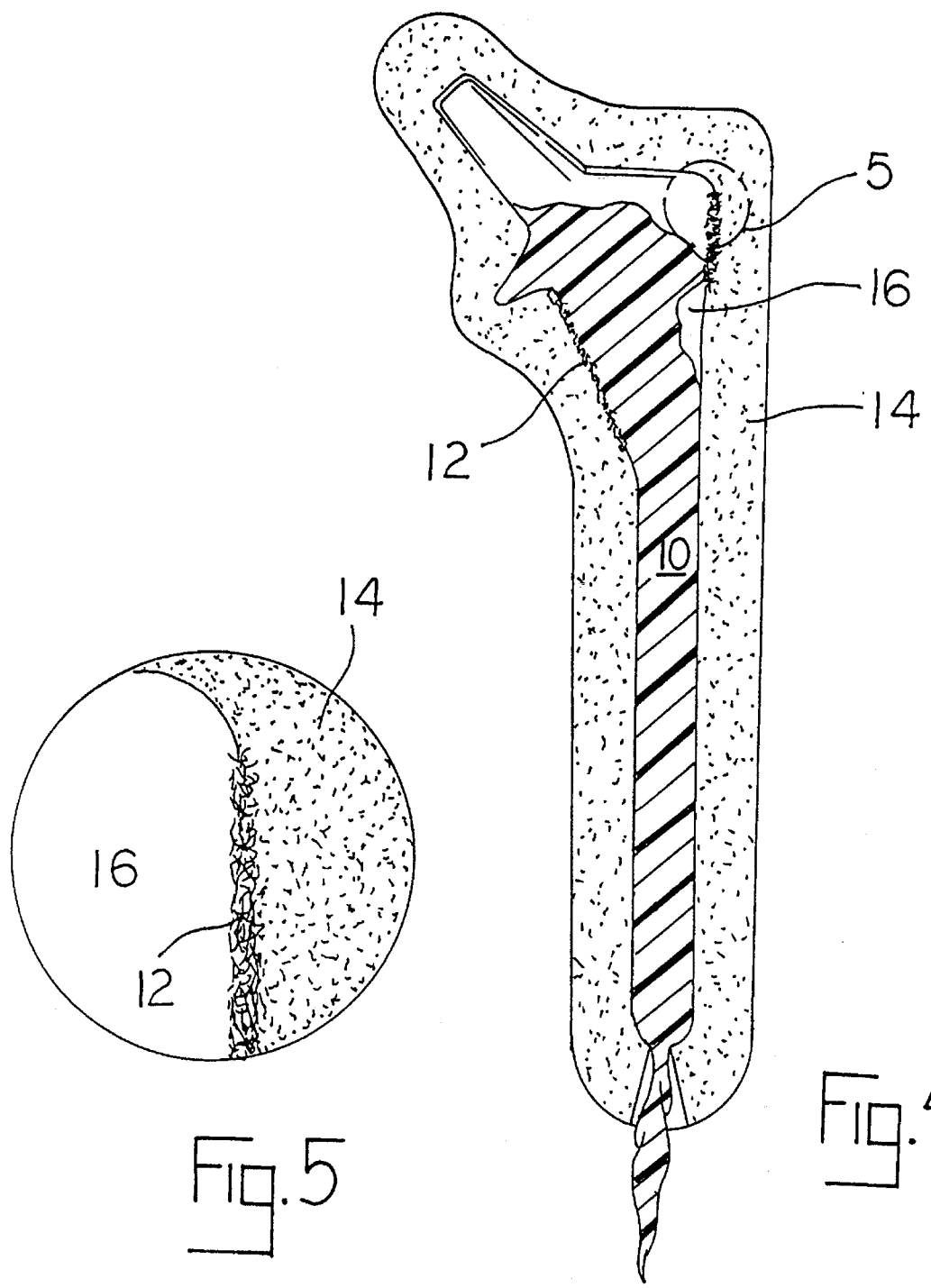

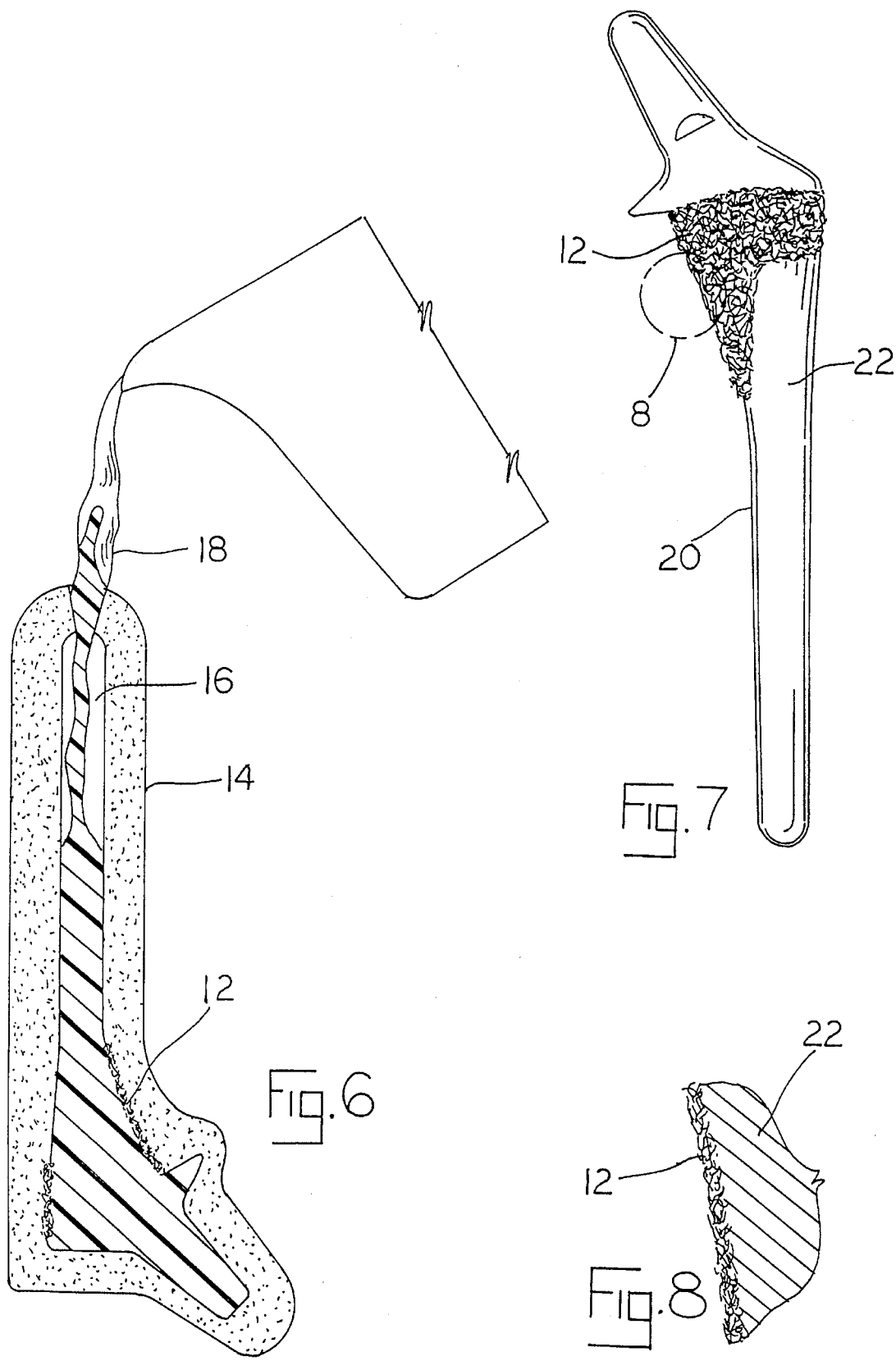

CAST ORTHOPAEDIC IMPLANT AND METHOD OF MAKING SAME

FIELD OF THE INVENTION

This invention relates to orthopaedic implants and methods of making orthopaedic implants and has special relevance to orthopaedic implants formed by casting.

BACKGROUND OF THE INVENTION

Orthopaedic implants used to replace a portion of the human anatomy can be formed in a variety of known materials using a variety of known manufacturing methods. For example, the implant may be machined from a block of titanium or may be forged from a cobalt chromium alloy. Implants may also be formed from an investment casting process wherein a positive mold is formed from wax and then coated with a ceramic shell investment to form a negative mold. After the wax is coated and the ceramic shell is hardened, the wax is melted out leaving the negative mold which is subsequently filled with molten metal. It is desirable in some implants to provide a porous outer surface for mechanical interlock with a bone cement or to provide an area for bone to grow into and thereby fix the implant to the bone. Typically, such porous surfaces take the form of a layer of small metal beads or a layer of metal mesh as are well known in the industry. The porous metal surface layer is typically metallurgically bonded to the implant body by diffusion bonding or sintering. Sintering is a joining process during which the melting point of at least one of the materials to be joined is slightly exceeded allowing formation of fluid metal which flows between the pieces to be joined effecting a physical metallic bond. Diffusion bonding is a similar process, but does not require a temperature in excess of any of the melting points of any of the materials to be joined. Pressure applied to compress the interface to be joined at a temperature generally slightly below melting is used to effect a physical bond due solely to solid state diffusion. Diffusion bonding a porous layer to an implant body can be a difficult manufacturing step especially when the implant surface is rounded or otherwise not flat. The procedure requires multiple diffusion bonding cycles each of which requires a strict compliance to temperature and pressure process parameters in order to ensure the porous layer is adequately bonded to the implant. Therefore, the diffusion bonding process consumes a great deal of the manufacturer's resources in the form of man hours and capital expenditures required.

SUMMARY OF THE INVENTION

This implant and method of this invention greatly reduces the amount of time and resources required to attach a porous surface layer to an implant body. The invention utilizes the investment casting process in a modified manner to provide a cast implant having a porous surface layer metallurgically bonded thereto. In the method of the invention, after the wax pattern of the implant is formed, the porous surface layer is formed about the wax pattern at the appropriate location. Preferably, the porous layer is pressed into or otherwise attached to the wax pattern so that a portion of the porous layer is interdigitated with the wax and becomes filled. Therefore, a portion of the porous layer remains exposed with its pores open and free from the wax. Alternatively, the wax or similar filler material could be impregnated to the porous layer to occlude or fill a portion of the pores prior to placing the porous layer in contact with the wax pattern. Next the wax pattern, with porous surface layer attached thereto, is coated in multiple layers of ceramic investment material to form the mold cavity in a known manner. During the coating process the portion of the porous layer not previously filled with wax is filled with the ceramic material. It may be advantageous to use a ceramic investment material that is biocompatible such as a hydroxyapatite or other calcium phosphates. Therefore, before the wax pattern is melted from the ceramic mold, a portion of the porous layer is filled with wax and the other portion of the porous layer is filled with the ceramic material. After the wax is melted from within the ceramic mold, a cavity is left in the shape of the implant. As for the porous layer, the portion previously filled with wax is now extending into the cavity and is exposed or, in other words, free from the filler wax material. After processing of the ceramic mold to harden the material, molten metal is poured into the mold to form the implant. The molten metal partially melts the exposed portion of the porous layer and thereby metallurgically bonds with the porous layer. Subsequent to cooling, the ceramic mold is cleaned away from the implant and the porous layer so that the portion of the porous layer previously filled with ceramic material is now exposed. The advantage of using a biocompatible coating as the investment can be seen at this stage of the process. Normally, it would be very important to remove all of the ceramic investment from the implant. It may be especially difficult to remove all of the investment from the porous surface. However, if the investment were biocompatible, residual investment left within the pores of the porous surface would not adversely affect the patient. In fact, if the investment were formed from hydroxyapatite, a known bone growth enhancer, it may be advantageous to leave the investment occluding the pores of the porous layer to promote bone growth therein when implanted.

In an alternative embodiment, the porous surface layer includes a thin metal barrier with porous material on each side thereof. The metal barrier layer serves to limit the interdigitation of the wax material. Further, the barrier serves to prevent intimate contact with the investment material and wax pattern in the area of the porous material to facilitate a more complete cleaning of the finished implant.

Accordingly, it is an object of the invention to provide for a cast implant having a porous surface layer formed during casting.

Another object of the invention is to provide for a method of forming a cast implant having a porous surface layer.

Another object of the invention is to provide for a method of making a cast implant with a porous surface layer using an investment casting process.

Yet another object of the invention is to provide for a method of forming a cast implant using an investment casting process wherein the wax pattern of the implant is covered by a porous surface layer prior to coating with ceramic investment material.

Still another object of the invention is to provide for a method of forming a cast implant using an investment casting process wherein investment material is biocompatible.

Other objects of the invention will become apparent upon a reading of the following description taken with the accompanying drawings.

BRIEF DESCRIPTION OF THE DRAWINGS

FIG. 1 is a perspective view of a wax pattern of an implant with a porous surface layer attached thereto.

3

FIG. 2 is an enlarged view with portions cut away of the area circled in FIG. 1 and illustrating the interdigitation of the wax into a portion of the porous surface layer.

FIG. 3 is an elevational view with portions cut away of the wax pattern with the porous surface layer coated in a layer of ceramic material.

FIG. 4 is the elevational view of FIG. 3 illustrating the wax pattern being melted away from the porous surface layer and ceramic to yield a cavity.

FIG. 5 is an enlarged view of the area circled in FIG. 4 illustrating the fiber metal having a portion exposed and extending into the cavity and a portion filled with ceramic material.

FIG. 6 is a view illustrating the ceramic mold with the porous surface layer being filled with a molten metal.

FIG. 7 is a perspective view of the finished implant after cooling and with the ceramic mold removed.

FIG. 8 is an enlarged and partially sectioned view of the area circled in FIG. 7 illustrating the junction between the porous surface layer and implant body.

FIG. 9 is an enlarged view of an alternative embodiment wherein the porous layer includes a barrier layer with porous material on each side thereof.

DESCRIPTION OF THE PREFERRED EMBODIMENTS

The following description of the preferred embodiment is not intended to be exhaustive or to limit the invention to the precise form disclosed. Rather, it is chosen and described so that others skilled in the art may utilize its teachings.

Referring now to the drawings, a wax replica or pattern 10 of an orthopaedic hip stem implant is illustrated in FIG. 1. It should be understood that a hip stem implant is shown purely for illustrative purposes and is not intended to be a limitation on the invention. FIG. 1 further illustrates a porous surface layer 12 wrapped about a portion of the wax pattern 10. The porous surface layer 12 as illustrated is formed from a metal wire mesh; however, such should not be considered a limitation to the invention. The porous layer may be formed from a variety of known materials such as metallic beads sintered to form a layer. The porous surface layer 12 is heated and pressed into the outer surface of the wax pattern 10 a predetermined amount so that a portion of the pores formed in the porous surface layer 12 are filled or otherwise occluded with the wax pattern material as is illustrated in FIG. 2. As illustrated, the outer portion of the porous surface layer is not impregnated with the wax and therefore retains its original porosity. It should again be understood that the precise shape or location of the porous surface layer 12 is not to be considered a limitation on the invention but is provided for illustrative purposes only. Next the wax pattern 10 with porous surface layer 12 attached is repeatedly dipped in a ceramic investment medium 14 and hardened in a well known manner to form the structure illustrated in FIG. 3. As the ceramic investment medium fills the outer pores of the porous surface layer so that after the ceramic mold is completely formed, a portion of the porous layer is filled with the wax pattern material and a portion of the porous layer is filled with the ceramic material. Therefore, upon completion of the ceramic mold, substantially all of the pores of the porous layer are filled with a filler material of either wax or ceramic medium. Next, as is common in the art of investment casting, the ceramic mold is heated to cure the mold and to melt away the wax pattern 10. As illustrated in FIG. 4, as the wax pattern 10 melts, the porous surface layer 12 is retained in position due to the interdigitation of the ceramic material into a portion of the porous surface layer. FIG. 5 illustrates that after the wax has been removed, the porous surface layer extends from the ceramic mold into the cavity 16 formed by the removed wax. After the wax pattern has been removed in a manner consistent with industry standards, molten metal 18 is poured into the ceramic mold as illustrated in FIG. 6 to fill the cavity 16 left by the wax pattern. The molten metal partially melts the exposed portion of the porous surface layer 12 which extends into the cavity 16. Therefore, the porous surface layer is metallurgically bonded to the implant due to the melt integration of a portion of the porous layer to the molten metal as illustrated in FIGS. 7 and 8. After the mold and metal have cooled, the ceramic mold is broken away from the implant in a known manner. Additionally, the pores of the porous layer previously filled with ceramic material are cleaned such that no ceramic residuals remain. The resulting implant 20 as illustrated in FIGS. 7 and 8 includes a metal body 22 having a porous surface layer 12 attached thereto.

As an alternative to the investment material normally used, the ceramic investment material could be formed from a biocompatible material such as hydroxyapatite or other calcium phosphates. The advantage being that if any of the biocompatible investment was left within the porous surface layer it would not adversely affect the patient. Further, the biocompatible investment material could be intentionally left within the porous surface to promote bone growth therein.

An alternative embodiment of the invention is illustrated in FIG. 9. In the alternative embodiment of FIG. 9, the porous layer 12' is formed to include a thin metal barrier layer 26 having porous material 28 bonded to each side thereof. In use, the barrier layer serves two functions. First, the barrier limits the amount of interdigitation of the porous layer into the wax mold, thereby ensuring a minimum thickness of the porous layer on the finished implant. Second, the barrier layer serves to prevent intimate contact between the investment material and the wax pattern along the porous surface layer. Preventing such intimate contact may assist in cleaning the investment material from the porous surface layer.

It should be understood that the invention is not to be limited to the precise forms disclosed, but rather, may be modified within the keeping of the appended claims.

We claim:

1. A method of making an orthopaedic implant having a porous surface layer attached thereto, the method comprising the steps of:

a. providing a replica of an orthopaedic implant formed from a first material;

b. attaching a porous layer formed from a second material to at least a portion of the replica, said porous layer having a plurality of pores therein; a first portion of the pores being filled with said first material;

c. coating said replica and porous layer with a third material, said third material filling a second portion of the pores of the porous layer;

d. removing said first material to form a cavity within said coating and thereby exposing said first portion of the pores;

e. filling the cavity with a fourth material such that said fourth material forms an integral bond with said porous layer adjacent said first portion of the pores; and f. removing the third material after the fourth material has solidified to thereby expose said second portion of the pores.

2. The method of claim 1 wherein said third material is biocompatible.

3. The method of claim 1 wherein said first material is wax, said second material is metal, said third material is a ceramic investment material and said forth material is molten metal.

4. The method of claim 1 wherein the porous layer is formed from a titanium fiber metal mesh.

5. The method of claim 1 wherein the porous layer includes a thin metal barrier with porous metal material bonded to first and second sides thereof, wherein the porous metal material on the first side of the metal barrier constitutes said first portion of the pores and the porous metal material on the second side of the metal barrier constitutes the second portion of the pores.

6. A method of forming a cast orthopaedic implant having a metal porous surface layer over a portion of the implant, the method comprising the steps of:

a. providing a wax pattern of an orthopaedic implant;

b. providing a metal porous surface layer having a plurality of pores;

c. pressing the metal porous surface layer into the wax replica such that a first portion of the plurality of the pores are filled with wax pattern;

d. coating the wax pattern with the metal porous surface layer attached thereto with a ceramic investment material to form a ceramic mold such that a second portion of the pores of the metal porous surface layer are filled with the ceramic investment material;

e. removing the wax pattern from the ceramic mold and thereby exposing the first portion of pores of the porous material;

f. filling the ceramic mold with molten metal, wherein the molten metal bonds with the porous metal surface layer adjacent the first portion of pores of the porous metal surface layer; and g. removing the ceramic mold after the molten metal has cooled.

7. The method of claim 6 wherein the porous metal surface layer includes a thin metal barrier layer with porous material bonded to first and second sides of the metal barrier, wherein the porous material bonded to the first side of the metal barrier constitutes said first portion of pores of the porous metal surface layer, the porous material bonded to the second side of the metal barrier constitutes said second portion of the pores of the porous metal surface layer.

8. The method of claim 6 wherein the ceramic investment material is biocompatible.

9. The method of claim 8 wherein a portion of the ceramic investment material is retained within the second portion of the pores of the porous metal surface layer after the ceramic mold is removed.

* * * * *